United States Patent
Baxter

(10) Patent No.: US 6,475,188 B1
(45) Date of Patent: Nov. 5, 2002

(54) BILATERAL MICROINJECTOR PUMP FOR FREELY MOVING ANIMALS IN AN OPERANT CHAMBER

(76) Inventor: Anthony David Baxter, 36 Cottage St., East Boston, MA (US) 02128

( * ) Notice: Subject to any disclaimer, the term of this patent is extended or adjusted under 35 U.S.C. 154(b) by 0 days.

(21) Appl. No.: 09/573,591

(22) Filed: May 18, 2000

Related U.S. Application Data

(60) Provisional application No. 60/135,150, filed on May 20, 1999.

(51) Int. Cl.[7] ............................................. A61M 37/00
(52) U.S. Cl. ........................ 604/131; 604/155; 417/572
(58) Field of Search .......................... 604/67, 131, 185, 604/117, 132, 151, 154, 155, 156; 204/299 R; 435/285.1; 417/572; 222/325

(56) References Cited

U.S. PATENT DOCUMENTS

| | | | | |
|---|---|---|---|---|
| 4,772,263 A | * | 9/1988 | Dorman et al. ............ | 604/132 |
| 4,790,823 A | * | 12/1988 | Charton et al. ............ | 604/136 |
| 4,898,579 A | * | 2/1990 | Groshong et al. ............ | 604/67 |
| 4,976,696 A | * | 12/1990 | Sanderson et al. ........... | 604/154 |
| 5,034,003 A | * | 7/1991 | Denance ..................... | 604/117 |
| 5,219,099 A | * | 6/1993 | Spencer et al. ............. | 222/325 |
| 5,238,654 A | * | 8/1993 | Nohl et al. .................. | 422/100 |
| 5,295,966 A | * | 3/1994 | Stern et al. .................. | 604/154 |
| 5,458,761 A | * | 10/1995 | Kamahori et al. ....... | 204/299 R |
| 5,656,034 A | * | 8/1997 | Kochersperger et al. ..... | 604/155 |
| 5,891,102 A | * | 4/1999 | Hiejima et al. ............. | 604/185 |
| 6,248,093 B1 | * | 6/2001 | Moberg ..................... | 604/131 |
| 6,251,658 B1 | * | 6/2001 | Henderson et al. ...... | 435/285.1 |
| 2002/0025267 A1 | * | 2/2002 | Lieber et al. ............... | 417/572 |

* cited by examiner

Primary Examiner—Teresa Walberg
Assistant Examiner—Leonid M Fastovsky

(57) ABSTRACT

A microinjection pump for unrestrained and freely behaving animals is provided. The microinjection pump employs a screw drive mechanism that is actuated by an attached small stepper motor. The pump moves fluid by direct mechanical displacement from two microsyringes arranged in parallel (see FIGS. 1 and 2). The pump pivots and turns freely above an animal cage by an electrical swivel and connects to the animal head only by two small flexible capillary tubes that store and deliver fluids to both sides of its brain. Through associated electronic connections, the pump allows the animal to lever press for self-administration of fluids.

2 Claims, 1 Drawing Sheet

BILATERAL MICROINJECTOR PUMP FOR FREELY MOVING ANIMALS IN AN OPERANT CHAMBER

Figure 1:
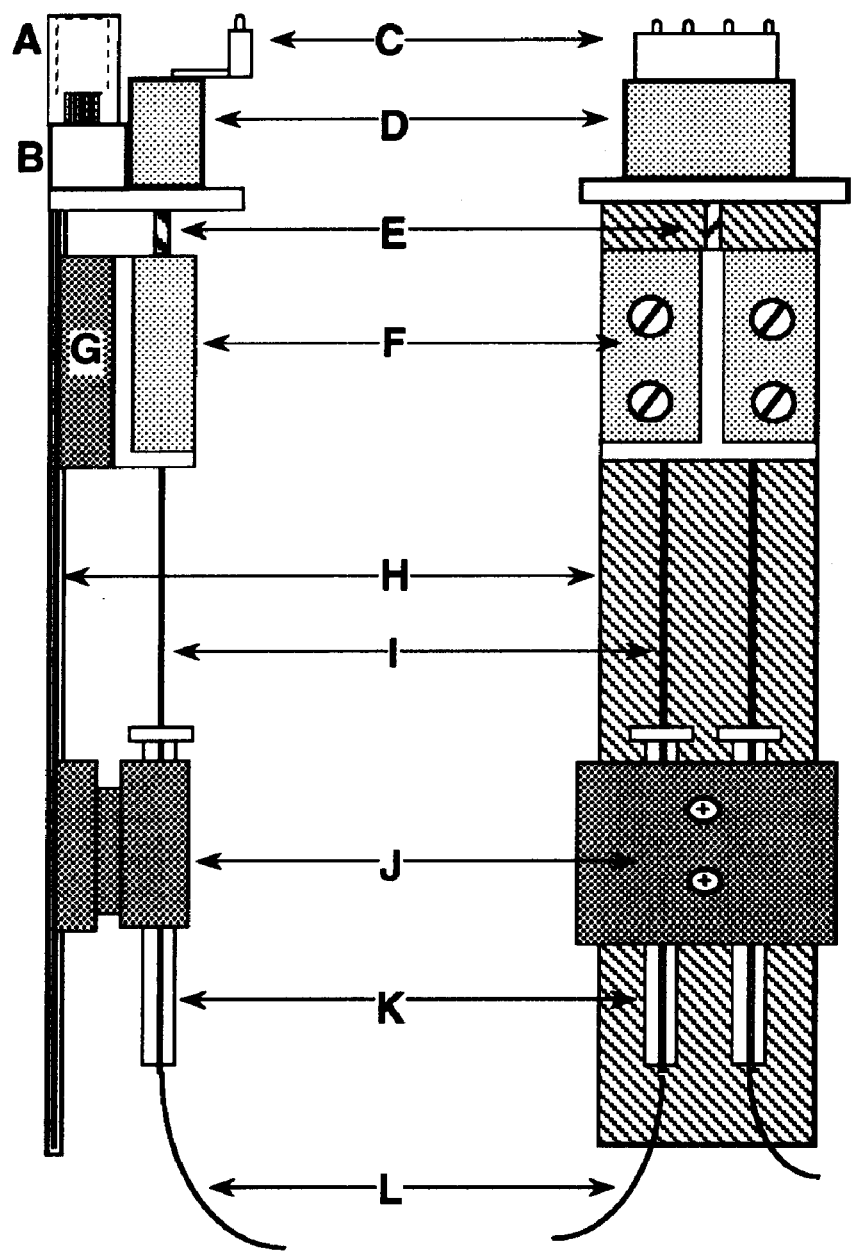

This application claims the benefit of Provisional Application Ser. No. 60/135,150, filed May 20, 1999.

BACKGROUND FOR THE INVENTION AND DEVELOPMENT OF THE BILATERAL MICO-INJECTOR PUMP

Procedures in behavioral pharmacology and neuroscience require bilateral intravenous and intra-cerebral micro-injections to be made into freely behaving and moving animals. For example, simultaneous drug administration to discrete populations of neurons within bilaterally paired sub-cortical regions avoids hemisphere-specific effects associated with unilateral injections and increases the chance of detecting the desired response. Also, animals can freely self-administer drugs without the stressful handling of humans. Because fluid swivel systems are not reliable at the volumes required for scientific studies in the fields mentioned above, I substituted an electrical swivel that allows for free movement of the micro-injector pump and the animal to which it is tethered by way of capillary tubing.

SPECIFICATION AND CLAIMS FOR THE BILATERAL MICRO-INJECTOR PUMP

My design, described herein, consists of a pump based on a screw drive mechanism. It contains a movable block that is connected to a ball bearing micro-slide (G, in FIG. 1 which includes all of the following letter referents). Block and slide form a unit called a knee (F). A rigid guide track and two microliter syringes complete the system. This bilateral micro-injection pump moves fluid by an indirect mechanical displacement method. It thereby eliminates many of the calibration uncertainties associated with pneumatic and electrolysis driven micro-injection systems, as well as those micro-injection systems based upon a fluid swivel.

The drive mechanism of the bilateral micro-injection pump is actuated by a small stepper motor (D). Associated electronics give a motor step size of either 7.5 or 15 degrees (48 or 24 steps per 360-degree revolution) as desired and programmed. The stepper motor turns a threaded rod (E, 0–80 screw approximately 3 inches long) that is soldered to the motor drive shaft and screwed into the block component of the movable knee (F), by way of a screw tapped hole. The knee is connected to the ball bearing slide via 4 small screws. The ball bearing slide is itself held to a rigid linear guide rail (H) by a groove running its entire length. The knee and ball bearing base together move linearly along the guide rail that prevents any rotational and/or lateral movement of the knee and slide. Together, the system of knee and ball bearing slide, converts the rotary motion of the stepper motor into precisely controlled linear motion and acts as a piston that mechanically displaces fluid from two microsyringes (K,), which are fixed on the guide rail by a clamp bracket (J). The knee depresses the plungers on the microsyringes (I) and causes the ejection of fluid out of the microsyringes and into the plastic capillary tubing (L) that deliver drug fluids to the freely behaving animal. By varying the number of steps of the stepper motor and thereby the linear distance traveled by the knee and the plungers of the microsyringes, the fluid amount delivered to the animal is precisely controlled and easily calibrated.

Power is delivered to the stepper motor through a modular (telephone) socket connector (B), and electrical circuitry connector (C). The entire pump assembly is suspended from a 4 channel commutator (D, handset cord untangler), attached via modular telephone plug/connector and telephone cord to the ceiling of the animal operant isolation chamber, and then to a microcomputer and an input/output device. The connection is made to the pump assembly by inserting the modular plug of the commutator into the modular socket of the connector (B), which is bolted to an L-shaped bracket that is screw bolted to the guide rail, and also holds the stepper motor. With this arrangement, the entire micro-injection pump assembly swivels freely, and since it is fully supported by the commutator, a counterweight is not needed.

I, therefore, assert that this bilateral micro-injection pump is, to the best of my understanding, the only one of its kind in the world. I claim that it performs the actions listed above and eliminates the need for a fluid swivel system for injecting fluids into freely moving animals, and, further, that it does this in a bilateral manner. This composition is unique and should be given a full Utility Patent and protected by all rights and laws.

This machine is currently on file under provisional patent application No. 60/135,150 filed May 20, 1999.

What is claimed is:

1. A recirculating micro ball bearing slide providing the frictionless mechanism for a movable block ( called a "knee" that is bolted to the ball bearing slide) and linear guide, providing the support and guide structure and housing for the knee and a stationary micro syringe holder and clamp; knee has a machined tapped hole in it for receiving a threaded rod; knee converts rotary motion of the turning threaded rod into its own linear motion along the guide rail; machined key slots on the knee receive and hold the plunger heads of two bilaterally arranged micro syringes; micro syringe clamp holds the barrels of the micro syringes stationary while the moving knee depresses the plungers in linear fashion causing extrusion of fluid from the micro syringes and into and through capillary tubing attached to the micro syringes for delivery of fluids into the freely behaving animal.

2. The microinjection pump, in accordance with claim 1, is actuated by a small stepper motor that is affixed to a flange that is itself bolted to the guide rail; power for the stepper motor is delivered through a 4 channel electrical "swivel" commutator and modular socket connector that is wired to the stepper motor; associated electronics give the motor step size of 15 degrees (24 steps per 360 degree revolution); the stepper motor drive shaft is attached to the threaded rod by a bolt and turns it in a rotary and stepwise manner; the threaded rod is screwed into the knee through the hole according to claim 1; the knee, held by the micro recirculating ball bearing slide and, through friction with the turning threaded rod, moves linearly along the guide and depresses the plungers of the micro syringes, extruding fluid in a stepwise, precise and accurate method; in reverse driving mode the stepper motor causes the knee to move in the opposite direction along the guide and retracts the micro syringe plungers and takes up fluid and fills the micro syringes.

* * * * *